United States Patent
Phan et al.

(10) Patent No.: US 7,069,155 B1
(45) Date of Patent: Jun. 27, 2006

(54) REAL TIME ANALYTICAL MONITOR FOR SOFT DEFECTS ON RETICLE DURING RETICLE INSPECTION

(75) Inventors: Khoi Phan, San Jose, CA (US); Bhanwar Singh, Morgan Hill, CA (US); Bharath Rangarajan, Sunnyvale, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 91 days.

(21) Appl. No.: 10/676,455

(22) Filed: Oct. 1, 2003

(51) Int. Cl.
- *G01B 5/28* (2006.01)
- *G06K 9/00* (2006.01)
- *H01L 26/00* (2006.01)

(52) U.S. Cl. .......... 702/35; 702/36; 382/149; 438/12

(58) Field of Classification Search ............ 702/35, 702/36, 128, 150, 155; 382/145, 149; 438/14, 438/5, 10, 12
See application file for complete search history.

(56) References Cited

U.S. PATENT DOCUMENTS

| | | | |
|---|---|---|---|
| 5,105,092 A * | 4/1992 | Natsubori et al. | 250/559.06 |
| 5,482,802 A * | 1/1996 | Celler et al. | 430/5 |
| 5,847,821 A * | 12/1998 | Tracy et al. | 356/237.1 |
| 6,383,715 B1 * | 5/2002 | Lu et al. | 430/270.1 |
| 6,566,885 B1 * | 5/2003 | Pinto et al. | 324/501 |
| 6,704,691 B1 * | 3/2004 | Chiou | 702/188 |
| 2005/0054115 A1 * | 3/2005 | Von Harrach et al. | 436/174 |

* cited by examiner

*Primary Examiner*—Bryan Bui
*Assistant Examiner*—Meagan S Walling
(74) *Attorney, Agent, or Firm*—Amin & Turocy, LLP

(57) ABSTRACT

The present invention generally relates to semiconductor processing, and in particular to methods and systems for analyzing photolithographic reticle defects that include detecting soft defects on a reticle and analyzing the material composition of the defects for a particular chemical signature. Specifically, the present invention scans and images a soft defect via an optical inspection scan of a reticle, mills the defect using a Focused Ion Beam, and analyzes the defect for signatures using Electron Spectroscopy for Chemical Analysis and/or Fourier Transform Infrared Spectroscopy. The present invention thus provides for real-time analysis of the chemical composition of a soft defect on a reticle without the need for a defect identification navigation system. According to an aspect of the present invention, reticle defects can be monitored without removal of a pellicle, thus facilitating increased throughput and decreased cost in reticle repair and/or cleaning. According to another aspect of the invention, signatures occurring in trace amounts can be removed via employing a Focused Ion Beam in a non-reactive gas environment.

24 Claims, 13 Drawing Sheets

REAL TIME ANALYTICAL MONITOR FOR SOFT DEFECTS ON RETICLE DURING RETICLE INSPECTION

TECHNICAL FIELD

The present invention generally relates to semiconductor processing, and in particular to methods and systems that analyze photolithographic reticle defects via detecting soft defects on a reticle and determining the material composition of the defects.

BACKGROUND OF THE INVENTION

As semiconductor trends continue toward decreased size and increased packaging density, every aspect of semiconductor fabrication processes is scrutinized in an attempt to maximize efficiency in semiconductor fabrication and throughput. Many factors contribute to fabrication of a semiconductor. For example, at least one photolithographic process can be used during fabrication of a semiconductor. This particular factor in fabrication processes is highly scrutinized by the semiconductor industry in order to improve packaging density and precision in semiconductor structure.

Lithography is a process in semiconductor fabrication that generally relates to transfer of patterns between media. More specifically, lithography refers to transfer of patterns onto a thin film that has been deposited onto a substrate. Transferred patterns then act as a blueprint for desired circuit components. Typically, various patterns are transferred to a photoresist (e.g., radiation-sensitive film), which overlies a thin film on a substrate during an imaging process described as "exposure" of the photoresist layer. During exposure, a photoresist is subjected to an illumination source (e.g. UV-light, electron beam, X-ray), which passes through a pattern template (e.g., a reticle) to print a desired pattern in the photoresist. Upon exposure to the illumination source, a radiation-sensitive quality of the photoresist permits a chemical transformation in exposed areas of the photoresist, which in turn alters the solubility of the photoresist in exposed areas relative to that of unexposed areas. When a particular solvent developer is applied, exposed areas of a photoresist are dissolved and removed, resulting in a three-dimensional pattern in the photoresist layer. Such pattern is at least a portion of the semiconductor device that contributes to final function and structure of the device, or wafer.

Efficient defect detection during lithography processes is an area of growing interest in the semiconductor industry. A defect in a patterned photoresist structure can be transferred to inferior layers of a semiconductor during a subsequent etch process in which the photoresist is employed. A defect or structural deformity can be the result of a defective reticle used to pattern the photoresist.

While wafer defect inspection systems have relatively high stage accuracy due to recent scrutiny of stage accuracy in wafer throughput, reticle defect inspection systems still lack an appreciable level of stage accuracy and are difficult to employ for analytical tests. Reticle defects can occur during fabrication of the reticle or during subsequent handling thereof, which can result in repeating wafer defects. A repeating wafer defect is one that occurs consistently on multiple wafers, as compared to a non-repeating defect, which affects a wafer individually. The danger associated with repeating defects is decreased throughput, and thus increased cost, in wafer production. Typically, a repeating defect indicates that a defect exists on the reticle, and not just on the wafer. With the increasing utilization of advanced reticle enhancement techniques, the effect of defects, even marginal defects, can be magnified when transferred to a wafer. If a photomask or reticle contains defects, even sub-micron in range, such defects can be transferred to a wafer during exposure. Defects on reticles can cause inaccurate patterns to form on the wafer. In addition, electrically active regions may not perform as desired, leading to an overall degradation of chip performance.

As the semiconductor industry continues to produce sub-micron and sub-half-micron design structures, the importance of reticle defect detection and improvements therein has become paramount. Reticle manufacture is governed largely by wafer critical dimension (CD), which is defined as the smallest allowable width of, or space between, lines of circuitry in a semiconductor device. As methods of wafer manufacture are improved, wafer CD is decreased, which in turn permits smaller reticle defects to slip past detection and be printed on a wafer. That is, reticle defects of a size that was once negligible are now capable of being printed on a wafer, resulting in reduced wafer yield and/or performance.

Soft defects on a reticle can arise, for example, from contact with a contaminated pellicle and/or from pellicle glue outgasing. Soft defects can also arise in many instances as a result of, for example, a sulfuric acid cleaning step during manufacturing of the reticle, and are typically comprised of a thin film of organic material. If a contaminant comprises, for example, sulfur, phosphorus, or amine(s), soft defect growth can be triggered upon exposure. Defects arising in this manner are often referred to as "adder" defects. Furthermore, soft defect growth is inversely proportional to wavelength value (e.g., the shorter the wavelength, the greater the rate of defect growth). As lithography processes become more refined, manufacturers employ shorter and shorter exposure wavelengths to reduce critical dimensions. This trend increases the risk of reticle soft defect growth, which in turn increases the probability that a defect will be printed on a wafer.

Conventional reticle inspection tools permit a user to inspect a reticle for soft defects and can provide some transmission data. For example, based on transmission loss associated with a particular inspection wavelength (e.g., 365 nm or 488 nm), a user can make a relatively informed decision regarding when to send a reticle back to the mask shop for cleaning and pellicle replacement. However, this is a destructive method whereby the pellicle must be removed for cleaning and then replaced by a new pellicle. For example, in a case where there is no sulfur or phosphorus signature in the reticle defect, a user can waste valuable resources attempting to correct a defect that is merely cosmetic. Furthermore, a repeating defect can be created via sulfuric acid cleaning processes performed on a reticle that otherwise initially had no sulfur signature, thereby adversely affecting throughput. Thus, there exists a need in the art for systems and methods that can improve soft defect detection in real time.

SUMMARY OF THE INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

The present invention provides for systems and methods for analyzing soft defects on a reticle during reticle defect inspection in real time without the need for a defect navigation system. If the reticle is associated with a pellicle, the present invention can detect and analyze defects in a non-pellicle region of the reticle. More specifically, the present invention provides for reticle soft defect chemical analysis via utilizing a chemical analysis component to analyze detected soft defects on a reticle in conjunction with a Focused Ion Beam (FIB). The FIB produces a finely focused ion beam, which can be directed at any particular spot on a reticle with high precision and can be rastered over an area of arbitrary size and shape.

The multi-functionality of the FIB in conjunction with a composition analysis tool is especially suited to semiconductor production because it permits a defect both to be imaged and manipulated. This is particularly important because, while not all reticle defects will adversely affect the finished device, it is difficult to make such a determination based solely upon knowledge of the existence of the defect. Rather, analysis of the composition of the defect facilitates a correct decision as to whether time should be sacrificed to unload a defective reticle and discard a recent batch of product or whether manufacture can continue despite a benign defect. Thus, the present invention permits analytical capability in reticle defect inspection without the need for a separate defect identification and navigation system. More specifically, the invention can determine whether sulfur, phosphorus, and/or amine(s) are present in a soft defect, which can result in adder defects over time.

According to one aspect of the present invention, chemical analysis of a soft defect can be performed to detect any extant sulfur signature in the defect. Although the present invention is described largely with regard to detecting sulfur signatures, it is to be understood that the invention can detect signatures associated with phosphorus, amine groups, or any other chemical compound capable of causing adder defect growth on a reticle. Scanning Electron Microscopy (SEM) can be utilized to image the reticle at a defect location. A FIB can be employed with a low beam current to scan and/or image reticle defects, or with a high beam current to cut a cross-section of the defect. The FIB is capable of cutting from either a top layer or a bottom layer. The utilization of the FIB to remove a thin layer of material from a defect ensures that the defect surface is clear of contaminants. Upon discovery of a soft defect, an Electron Spectroscopy Chemical Analysis (ESCA) beam can be employed to determine the material composition of the soft defect. The information acquired during analysis can be fed to a processor for determination of the chemical composition of the defect. According to a particular aspect of the invention, the ESCA specifically analyzes the defect for a sulfur signature. If a sulfur signature is found, the system can alert a user to remove the reticle for cleaning and/or repair. Additionally, the system can inform a user of the presence of sulfur on the reticle and permit the user to make a determination of whether the reticle requires cleaning and/or repair.

According to another aspect of the invention, a Fourier Transform Infrared Spectroscopy (FTIR) beam can be employed to determine the chemical composition of a soft defect in the event that the defect is larger than a predetermined value, for example greater than 100 microns in diameter. Larger defects can ultimately be removed using conventional methods. However, the presence of sulfur, phosphorus, etc., signatures is highly indicative of the presence of such elements and/or compounds between the reticle and pellicle. Knowledge of such a contaminant(s) between a pellicle and a reticle can facilitate making a more educated decision regarding whether to remove a reticle from a stepper for cleaning and/or rejection, which in turn permits resources to be expended more wisely.

According to another aspect of the invention, when a sulfur signature of relatively small magnitude (e.g., on the order of parts per billion) is detected, the present invention can utilize a FIB in conjunction with a non-reactive gas environment to effectuate a phase shift in the sulfur from solid to vapor. A chamber in which the non-reactive gas is can be continuously pump-out to remove sulfur as it enters the vapor phase.

According to yet another aspect, the invention can employ closed loop feedback to monitor soft defect growth. For example, if a signature is detected that is not immediately detrimental to reticle performance, a decision can be made to leave the defective reticle in the stepper. According to this aspect, a chemical analysis component can scan the defect at predetermined intervals and/or continuously. Data from the scans can be processed and analyzed to facilitate adjusting a prediction regarding reticle life. For example, the growth rate of a soft defect may indicate that the reticle may be successfully employed for a certain period, the end of which is delineated by an unacceptably high potential for a fault condition.

One significant application of these systems and methods of soft defect detection and correction is in optical lithographics, commonly utilized in the manufacture of integrated circuits such as semiconductor memory devices, microprocessors, and other integrated circuits. Other applications include the manufacture of compact discs and other laser-readable memory devices. The systems and methods of the present invention can be employed to detect and correct defects on reticles and/or photomasks used not only in conjunction with the above applications, but also for wiring patterns, word lines, bit lines, whole lines, and black patterns. Furthermore, the application of this invention can be utilized in other applications requiring fine-line reticles or photomasks.

To the accomplishment of the foregoing and related ends, certain illustrative aspects of the invention are described herein in connection with the following description and the annexed drawings. These aspects are indicative, however, of but a few of the various ways in which the principles of the invention can be employed and the present invention is intended to include all such aspects and their equivalents. Other advantages and novel features of the invention will become apparent from the following detailed description of the invention when considered in conjunction with the drawings.

DETAILED DESCRIPTION OF THE INVENTION

Figure 1:
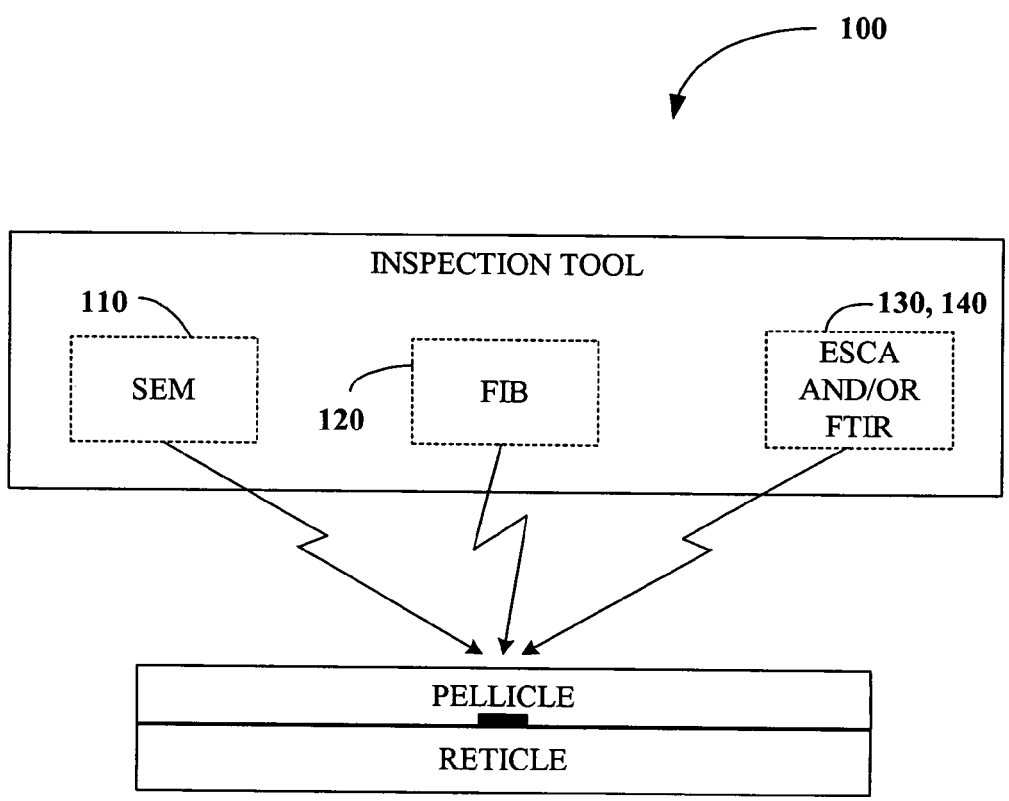
FIG. 1 is an illustration of a block diagram of a reticle soft defect inspection and/or correction tool in accordance with an aspect of the invention.

The present invention will now be described with reference to the drawings, wherein like reference numerals are used to refer to like elements throughout. The present invention will be described with reference to a system for inspecting and/or correcting reticle defects in real time. It should be understood that the description of these exemplary aspects are merely illustrative and that they should not be taken in a limiting sense.

The term "component" refers to a computer-related entity, either hardware, a combination of hardware and software, software, or software in execution. For example, a component can be a process running on a processor, a processor, an object, an executable, a thread of execution, a program and a computer. By way of illustration, both an application running on a server and the server can be components. A component can reside in one physical location (e.g., in one computer) and/or can be distributed between two or more cooperating locations (e.g., parallel processing computer, computer network).

It is to be appreciated that various aspects of the present invention can employ technologies associated with facilitating unconstrained optimization and/or minimization of error costs. Thus, non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks and function link networks can be employed.

FIG. 1 is an illustration of a block diagram of a reticle defect inspection and/or correction system 100 in accordance with an aspect of the invention. The inspection and/or correction system 100 comprises a Scanning Electron Microscope (SEM) 110 that scans a reticle for defects and can image a soft defect at a defect location; a Focused Ion Beam (FIB) 120 that can cut a layer from a soft defect to ensure that the defect is free of contaminants; and an Electron Spectroscope for Chemical Analysis (ESCA) 130 that can determine the presence of, for example, a sulfur signature in the chemical composition of a soft defect. According to another example, where the detected defect is relatively large in size, for example, greater than 100 microns in diameter, a Fourier Transform Infrared Spectroscope (FTIR) 140 can be employed, in addition to or in place of the ESCA 130, to determine whether a sulfur signature is present in the chemical composition of the defect. Although the present invention is described herein largely with reference to a "sulfur signature," it is to be appreciated that aspects of the invention permit detection of signatures associated with phosphorus, amine groups, or any other signatures that can be capable of causing adder defect growth.

According to an aspect of the present invention, the inspection system is employed to detect the physical presence of, and analyze the chemical composition of, a soft reticle defect without requiring a defect identification and/or navigation system. The present invention can facilitate making a most-correct determination of, for example, when a reticle should be removed for cleaning. For instance, if a pellicle is associated with the reticle, the system 100 can scan the non-pellicle side of the reticle for appropriate signatures. The presence of, for example, a sulfur signature on the non-pellicle side of a reticle is a strong indicator that sulfur is present between the pellicle and the reticle. Knowledge of a heightened probability that sulfur is present between the reticle and the pellicle can facilitate making a decision to remove the reticle for cleaning. Additionally, if a reticle is free of defects comprising sulfur and/or any other contaminant that can cause soft defect growth, a more educated decision can be made to continue wafer production. According to this example, a decision to proceed with Advanced Process Control (APC) can be made based on the fact that no detrimental signatures are detected.

To further the above examples, if information provided by the SEM 110 indicates the existence of a defect, then the FIB 120 can scan the defect to obtain further information regarding the structure, shape, and or size of the defect. When a lower beam current, for example 6 pA, is employed by the FIB 120, the FIB 120 can image the reticle at resolutions equivalent to those of the SEM 110. The FIB 120 system can image a reticle via utilizing either secondary electrons or secondary ions, both of which are byproducts of the ion beam. Images generated using FIB 120 secondary electrons can be viewed at high grain orientation contrast, permitting grain morphology imaging without the need for chemical etching. Images generated using FIB 120 secondary ions can be utilized to reveal chemical differences existing within the scanned sample. These features of the FIB 120 make the employment of the separate SEM 110 optional, depending on the user's particular needs.

Another advantage of employing the FIB 120 is that the FIB 120 can mill or cut the defect at a top layer or at a bottom layer of the defect, permitting excision of a portion of the defect in well-defined localized geometries. This feature also permits the FIB 120 to cut a thin layer from the defect in order to ensure that the surface of the defect is free of contaminants, which advantageously ensures that accurate information will be returned by the chemical composition analyzer (e.g., the ESCA 130 and/or the FTIR 140).

Once a soft defect has been cut by the FIB 120, the ESCA 130 analyzes the chemical composition of the defect to determine whether a sulfur signature is present. For example, the ESCA 130 can employ a monochromatic X-ray beam to measure the kinetic energy of electrons emitted by the defect. In this scenario, the photoelectric effect is responsible for the emission of core electrons by the sample. The kinetic energy of the X-ray beam is a known quantity, as is the work function of the ESCA 130. Once the kinetic energy of the core electrons is quantified, the binding energy of the electrons can be mathematically determined by the following formula:

$$E_B = E_{k_{Xray}} - E_k - f(w)$$

where $E_B$ is the binding energy of a given electron, $E_{k_{Xray}}$ is the kinetic energy of the monochromatic x-ray beam, $E_k$ is the measured kinetic energy of the electron, and f(w) is the work function of the instrument. Since each element has a unique binding energy, the binding energy of the emitted electron can be utilized to identify the element from which the electron was emitted, thereby permitting identification of the elemental composition of the defect. Typically, binding energy is plotted against intensity in the energy spectrum, and peak intensities are deterministic of elemental surface composition.

According to another aspect of the present invention, Fourier Transform Infrared Spectroscopy (FTIR) 140 can be employed in addition to or in place of the ESCA 130 to determine the chemical composition of the defect when the defect is larger than a predetermined value, for example, greater than 100 microns.

The FTIR 140 measures molecular bond vibration frequency in the defect. There are several frequencies at which a given molecular bond can vibrate: the lowest frequency is the ground state (G), and the higher frequencies are known as excited states (E). By exposing a molecular bond to infrared light, the FTIR 140 causes the bond to absorb light energy and become excited. The difference of the two energy states involved is always equal to the energy of the light absorbed. That is, $$E - G = \frac{hc}{l}$$

where h is Planck's constant, the energy stored in a single photon ($6.626 \times 10^{-34}$ Joule-seconds), c is the speed of light (299,792, 458 meters/second), and $\lambda$ is the wavelength of the light absorbed. In this manner, the FTIR 140 can determine what molecular bonds are present in the defect material and can determine the identity of elements bonded thereby. If the defect is detrimental, the present invention can employ conventional means to remove the defect, such as employing the FIB 120 to excise all or part of the defect, for example.

It is to be appreciated that the SEM 110 utilized by the present invention can be, for example, a Field Effect Scanning Electron Microscope (FESEM), an In-Lens FESEM, or a Semi-In-Lens FESEM, depending on the desired magnification and precision. For example, FESEM permits greater levels of magnification and resolution at high or low energy levels by rastering a narrower electron beam over the sample area. FESEM thus permits quality resolution at approximately 1.5 nm. Because FESEM can produce high-quality images at a wide range of accelerating voltages (typically 0.5 kV to 30 kV), it is able to do so without inducing extensive electrical charge in the sample. Furthermore, conventional SEM cannot accurately image an insulating material unless the material is first coated with an electrically conductive material. FESEM eliminates the need for the deposit of an electrically conductive coating prior to scanning. According to another example, the SEM component of the present invention can be In-Lens FESEM, which is capable 0.5 nm resolution at an accelerating voltage of 30 kV, or any other suitable type of scanner, such as Transmission Electron Microscopy (TEM), Atomic Force Microscopy (AFM), Scanning Probe Microscopy (SPM), etc.

It is further to be appreciated that the FIB component 120 of the present invention can be either a single ion beam FIB or a dual-beam FIB. For example, a dual-beam FIB can comprise an electron beam and an ion beam, thereby embracing dual functionality as a scanning electron microscope and a focused ion beam. According to this aspect of the present invention, the separate SEM component 110 can be optional. It is to be understood that discussion of the "SEM" or "SEM component" as it pertains to the present invention can refer to either a separate and distinct SEM component or to the SEM functionality of a dual-beam FIB component.

It is further to be appreciated that the chemical analysis component 130, 140 of the present invention can be, for example, Energy Dispersive X-Ray Spectroscopy (EDS). EDS operates by collecting the X-ray fluorescence generated by the interaction between the SEM scanner and the atoms being scanned thereby. The EDS then sorts the incoming X-rays according to their relative energy levels and plots them accordingly. The peaks on the plotted graph are associated with distinct energy levels, which in turn are correlated to the elements they represent. In this way, EDS can determine the chemical composition of the sample scanned by the SEM 110 component. Conventional EDS can only identify elements with an atomic number of 6 or greater: thus the chemical composition of defects comprising Boron, Beryllium, Lithium, Helium, and/or Hydrogen cannot be accurately identified using EDS. However, the present invention is concerned with detecting sulfur signatures (atomic number 16), and is therefore not affected by this limitation of EDS.

According to another aspect of the present invention, the chemical analysis component 130, 140 of the present invention can be, for example, Wavelength Dispersive X-Ray Spectroscopy (WDS). WDS has several important advantages over EDS. Among these are increased sensitivity and spectral resolution, especially with respect to the light elements mentioned above. However, EDS is more commonly applied than WDS due to its greater speed and simplicity. According to yet another aspect of the present invention, the chemical analysis component can be Scanning Auger Analysis (SAM), which can identify elements with an atomic number greater than that of Helium. These examples are given by way of illustration only and are not intended to limit the scope of the present invention.

Figure 2:
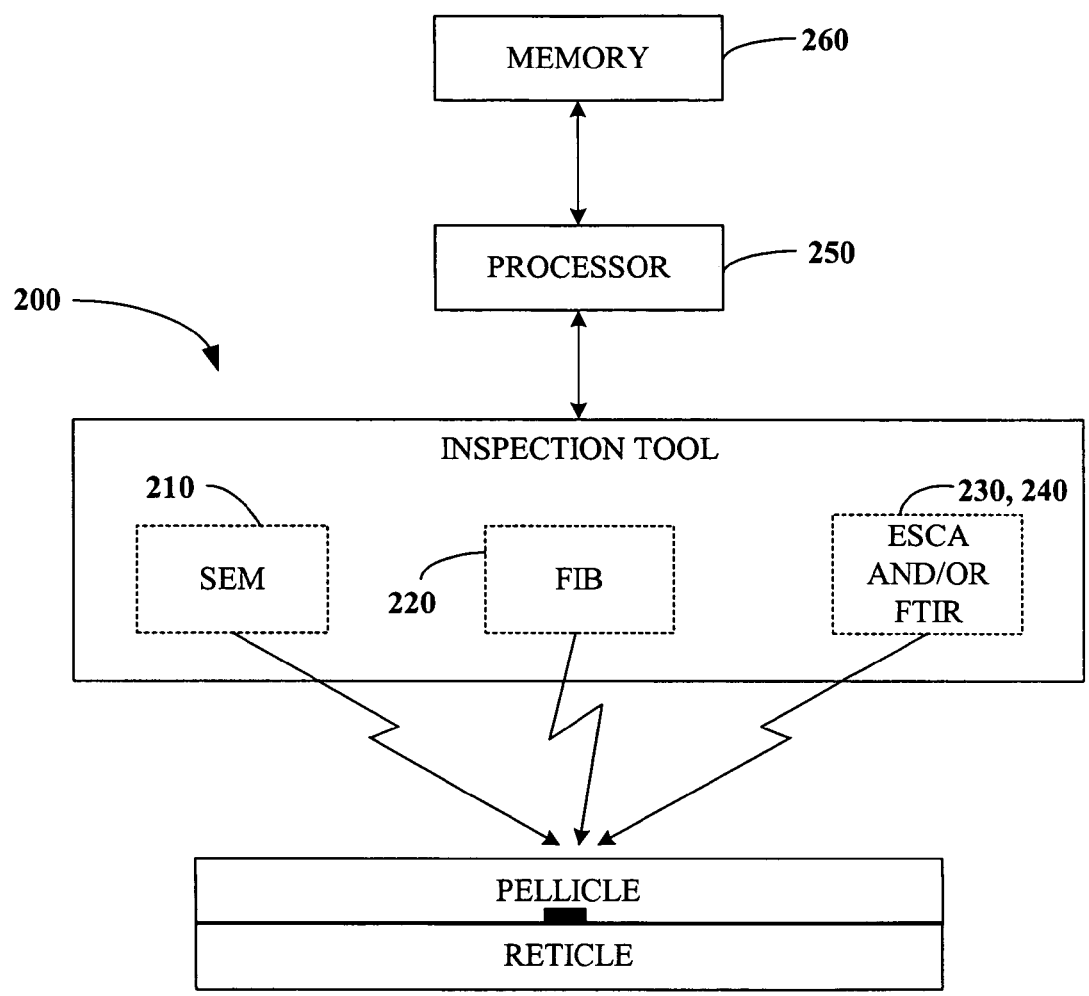
FIG. 2 is an illustration of a block diagram of a reticle soft defect inspection and/or correction system in accordance with an aspect of the invention.

FIG. 2 is an illustration of a block diagram of a reticle defect inspection and/or correction system in accordance with an aspect of the invention. The inspection system 200 comprises an SEM 210, an FIB 220, and an ESCA 230, operatively coupled to permit inspection, analysis, and correction of reticle defects without requiring a defect identification or navigation system. In one example, the ESCA 230 can be replaced or supplemented by a FTIR 240. According to an aspect of the present invention, a processor 250 operatively coupled to the defect inspection system 200 directs the system 200 to scan the sample reticle. The processor 250 is operatively coupled to a memory 260. It is to be understood that a that the processor 250 can be a processor dedicated to determining whether defects and/or contaminants exist, a processor used to control one or more of the components of the inspection and/or correction system, or, alternatively, a processor that is both used to determine whether defects and/or contaminants exist and to control one or more of the components of the inspection and/or correction system. The memory 260 can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), or flash memory Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory 260 of the present Systems and methods is intended to comprise, without being limited to, these and any other suitable types of memory.

According to one example, the memory 260 can store information related to schedules for maintenance and/or replacement on reticles. For instance, if a sulfur signature is detected on a reticle, but no adder defect growth is evident, the invention can proceed with APC based on stored information tables that can be predictive of a most appropriate time for reticle maintenance and/or removal. Such information can be based on, for example, average life-expectancy of a reticle, number of exposure pulses, etc.

Additionally, a feedback/feed-forward loop can be maintained between the chemical analysis component 230, 240 and the processor 250 and memory 260 in order to adjust predictions of a most appropriate time for reticle removal and/or maintenance based on continuous and/or periodic measurements of a soft defect. To further this example, if a sulfur signature is present in a soft defect but no substantial defect growth has yet occurred, a decision can be made to leave the reticle in the stepper. Measurements of the soft defect can be taken, for example, every 100,000 pulses of an exposure source. The system 200 can thereby monitor growth of a soft defect and predict a point at which the defect will adversely affect wafer throughput (e.g. cause a fault condition), thereby enabling the system to more accurately predict an adjusted most appropriate time for reticle removal and/or maintenance.

According to another aspect of the invention, the system 200 can remove signatures of smaller magnitudes. For example, if a sulfur signature is on the order of a few parts per billion, the system can employ the FIB 220 in conjunction with a non-reactive gas environment (not shown) to effectuate a phase shift in the sulfur from solid to vapor form. Once the sulfur is in vapor form, a continuous pump-out of the treatment chamber (not shown) permits the sulfur to be removed from the environment. Thus, the invention can advantageously effect a treatment of a detrimental signature.

Figure 3:
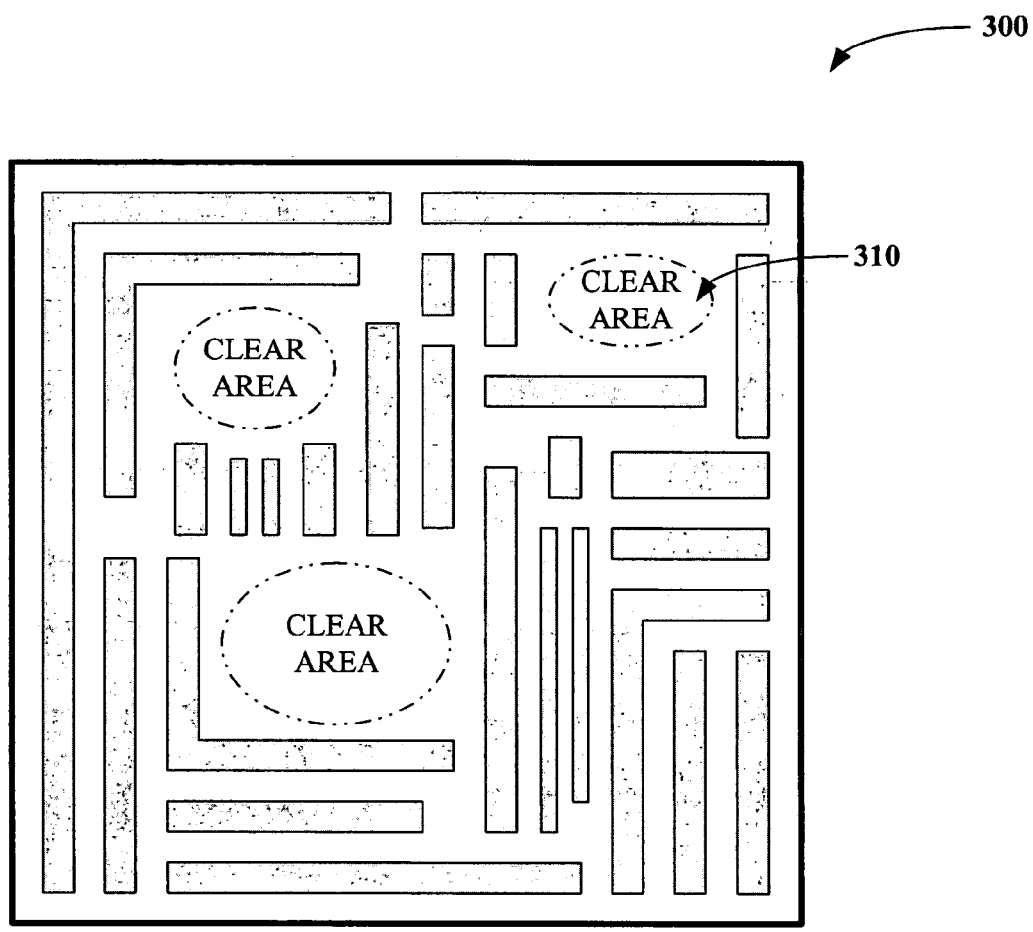
FIG. 3 is an illustration of an exemplary reticle.

FIG. 3 is an illustration of an exemplary reticle 300 (e.g. photomask) typical of the type used in a lithographic imaging system. In semiconductor integrated circuit fabrication, a reticle is utilized during the lithographic imaging process to expose a resist layer coated on a semiconductor substrate. Such exposure permits the pattern formed on the reticle to be transferred to the resist layer on the substrate. The reticle 300 as illustrated is a brightfield reticle wherein patterned features to be transferred are opaque features on a transparent or translucent background. However, it is to be understood that the principle and process of the invention can be applied to a darkfield reticle, wherein the patterned features to be transferred are clear features on an opaque background. Reticle substrate 310 can be silica glass, fused quartz, or any other material suitable for use in semiconductor lithographic operations. When a substrate is exposed to an exposure source, light passes through the clear areas of the reticle 300 to cause a chemical transition in the resist. Only the exposed areas of the resist undergo the chemical reaction, which results in a solubility gradient between the exposed portions of the resist and the unexposed portions. When the critical dimension of the reticle is considered, it becomes readily apparent that a defect even a half-micron in diameter can have deleterious effects on the performance of the integrated circuit.

Figure 4:
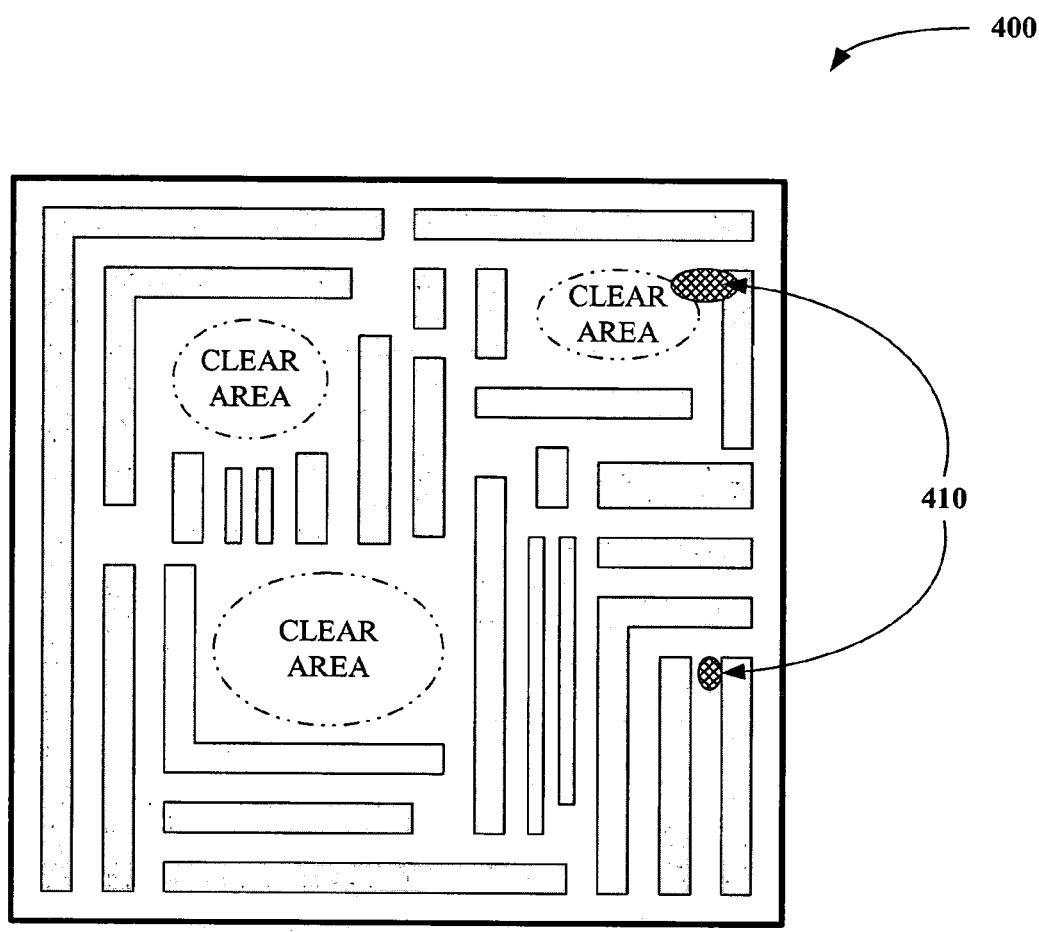
FIG. 4 is an illustration of a reticle with soft defects.

FIG. 4 is an illustration of a reticle 400 with soft defects 410. A typical soft defect is a thin film of organic material that can result from, for example, contact with a pellicle, pellicle glue outgasing, cleaning during manufacturing, etc. If the cleaning agent(s) and/or contaminant(s) comprise sulfur, phosphorus, and/or amine(s), then defect growth (e.g., adder defects) can occur during successive exposures. Furthermore, lower wavelength exposure sources cause more rapid defect growth than higher wavelength exposure sources (e.g., 193 nm causes more defect growth than 248 nm, which in turn causes more growth than 365, etc.). Soft defects can occur on chromium surfaces that are protected by a pellicle, as well as on glass surfaces that are not protected by a pellicle. Such soft defects can result in the printing of improperly connected lines on the substrate, which will ultimately disrupt the performance of the finished product.

Figure 5:
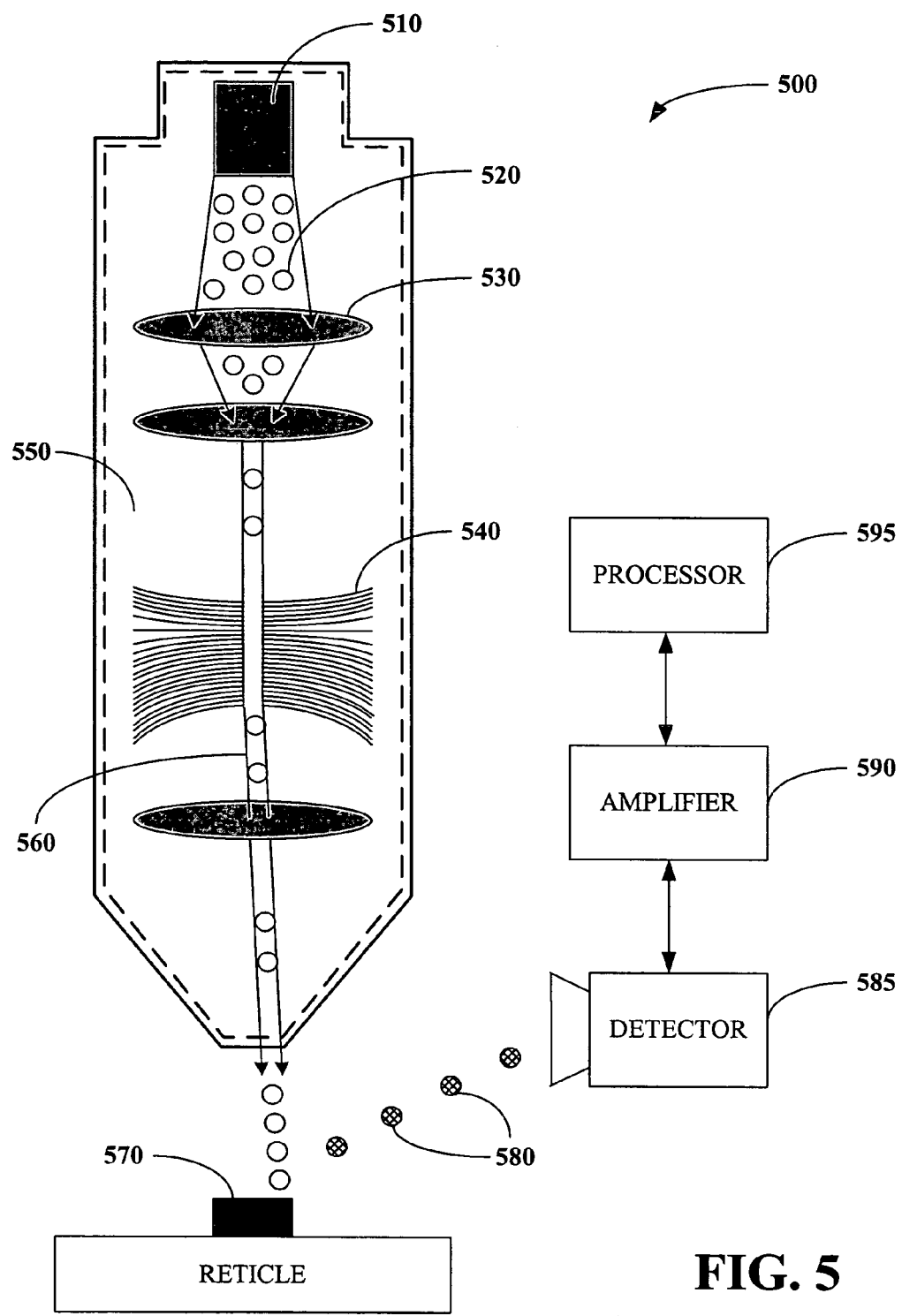
FIG. 5 is an illustration of a typical Scanning Electron Microscope (SEM) for use in a defect inspection tool in accordance with an aspect of the invention.

FIG. 5 is an illustration of a typical SEM tool 500, as described with reference to FIGS. 1 and 2. The SEM employs an electron gun 510 to fire high-energy electrons 520 through a series of magnetic lenses 530 and coils 540 contained in a vacuum column 550 to achieve a finely focused electron beam 560. In order to scan the defect, the magnetic coils 540 within the vacuum chamber 550 deflect the beam 560 and raster it back and forth over the defect 570. When the high-energy electrons 520 in the beam collide with the sample area of the defect 570, secondary electrons 580 are released by the defect 570 and counted by a detector 585, which in turn transmits the signals through an amplifier 590 to the processor 595. An image is created based on the number of secondary electrons 580 released from a given sample area of the defect 570 during the scan. The FIB component of the present invention operates in similar fashion, by employing an "ion gun." A dual-beam FIB operates in the same fashion but is capable of firing electrons or ions, thus performing the functions of both the SEM and the single-beam FIB described above. It is to be understood that discussion of the "SEM" or "SEM component" as it pertains to the present invention can refer to a separate and distinct SEM component or to the SEM functionality of a dual-beam FIB component.

Turning briefly to FIGS. 6, 7, 8, 9, and 10, methodologies that can be implemented in accordance with the present invention are illustrated. While, for purposes of simplicity of explanation, the methodologies are shown and described as a series of blocks, it is to be understood and appreciated that the present invention is not limited by the order of the blocks, as some blocks can, in accordance with the present invention, occur in different orders and/or concurrently with other blocks from that shown and described herein. Moreover, not all illustrated blocks may be required to implement the methodologies in accordance with the present invention.

Figure 6:
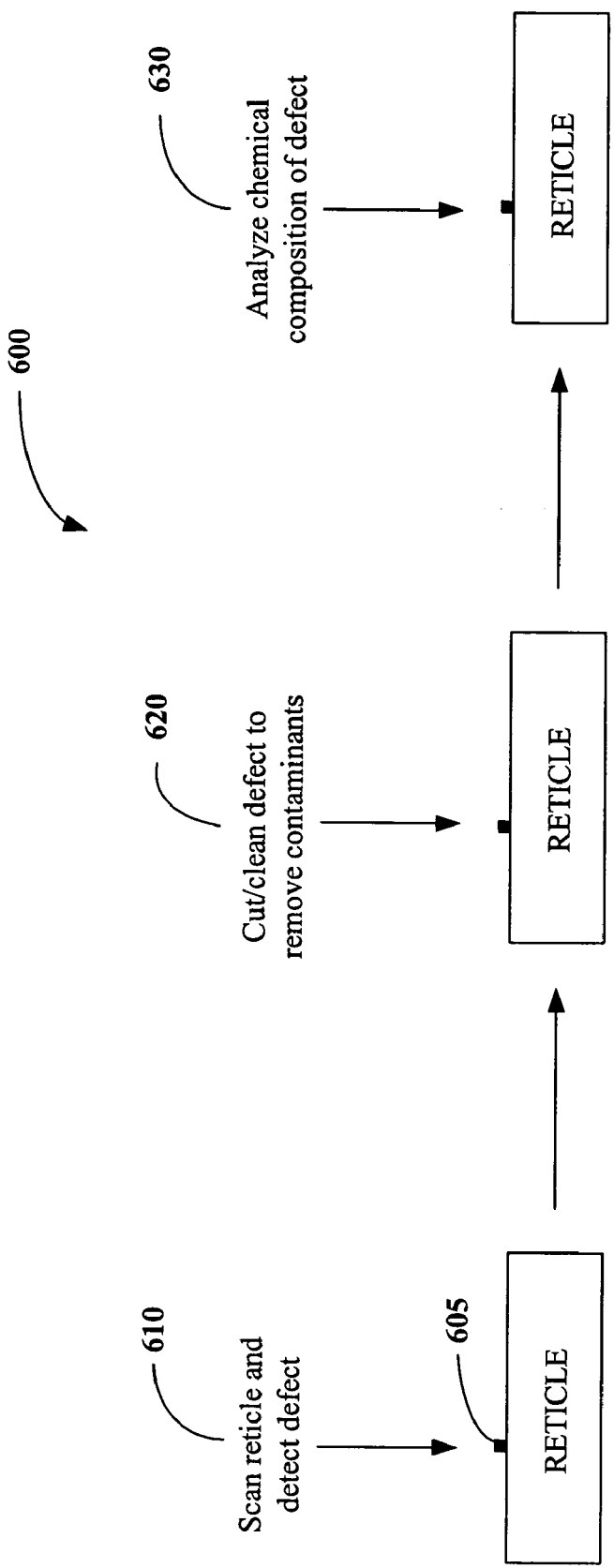
FIG. 6 is an illustration of a methodology for inspecting and/or analyzing a soft defect on a reticle in accordance with an aspect of the invention.

FIG. 6 is an illustration of a methodology 600 in accordance with an aspect of the present invention wherein a reticle having a potential defect 605 is first exposed to a scanner at 610, for example an SEM. The defect 605 undergoes a milling or cutting act at 620, which ensures a clean surface for chemical analysis. The reticle is exposed to a chemical analysis component at 630, for example an ESCA and/or FTIR, to determine whether sulfur, phosphorus, or amine signatures are present in the chemical composition of the defect. The presence of a signature can be indicative of the presence of other signatures between the reticle and an associated pellicle, which can facilitate making a more educated decision regarding a most appropriate time for removing and/or cleaning the reticle.

Figure 7:
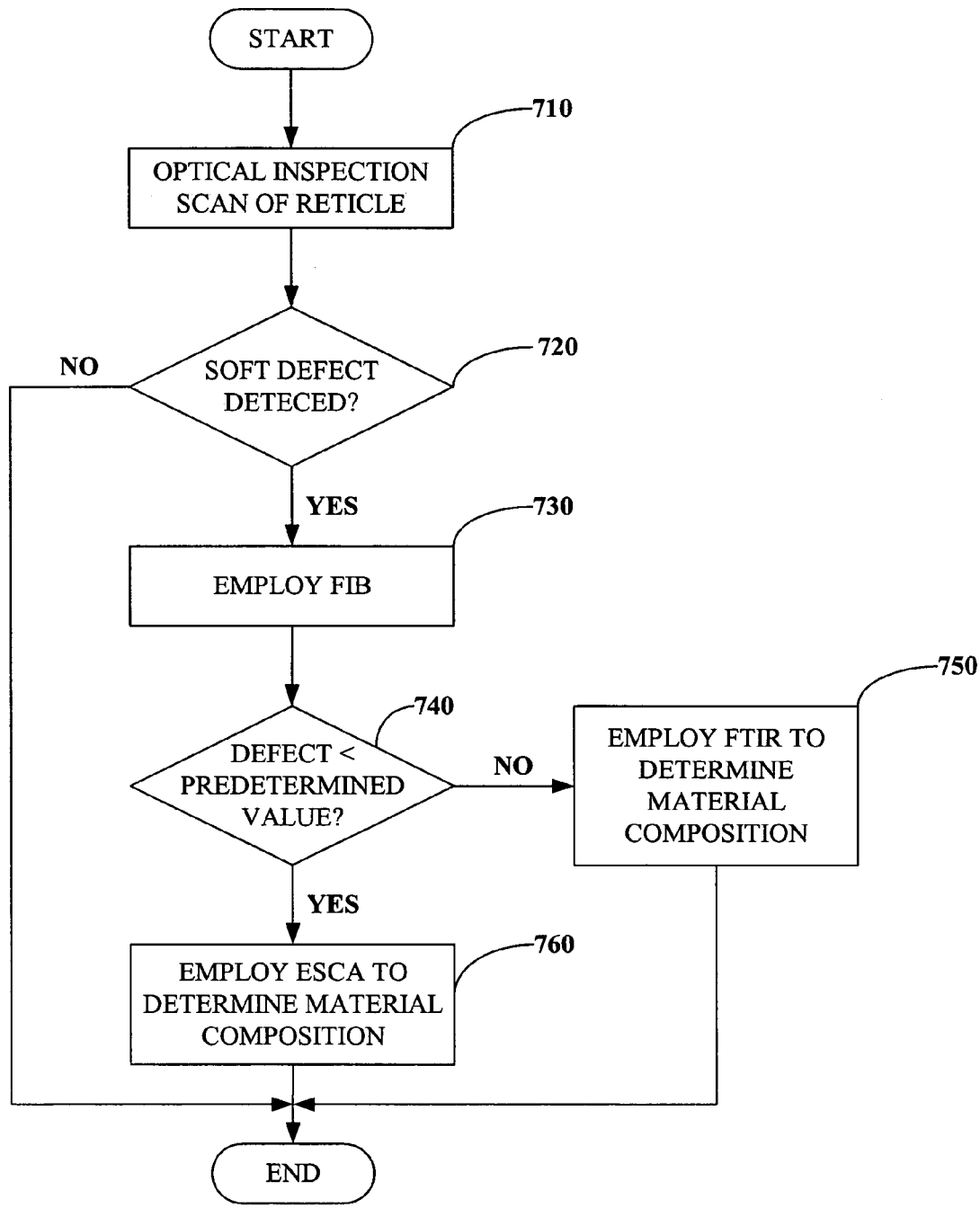
FIG. 7 is an illustration of a flow diagram of a methodology for inspecting and/or analyzing soft defects on a reticle in accordance with an aspect of the invention.

FIG. 7 is an illustration of a methodology 700 for inspecting a reticle in accordance with an aspect of the invention. The methodology begins with an SEM scan of the surface of a non-pellicle region of a reticle at 710. At 720, an inquiry is made as to the existence of a soft defect. If no defect is discovered, then the system can refrain from gathering further information and approve the reticle. If the SEM scan produces information indicative of the presence of a soft defect, then a FIB is employed at 730 to provide a precision cut in a "cleaning" act. Such a precision cut will maximize the effectiveness of the chemical analysis tool by ensuring that the surface of the soft defect to be analyzed is free of contaminants. After the FIB acts upon the reticle, an inquiry is made as to whether the soft defect is larger than or smaller than a predetermined value, for example 100 microns, at 740. If the defect is of a relatively large size, FTIR can be employed to analyze the material composition of the defect at 750 to determine whether a sulfur signature is present. If the size of the defect is below a predetermined value, then ESCA can be employed to analyze the material composition of the defect at 760.

According to another example, if the information provided by the SEM scan at 710 suggests that no defect is present, the FIB can still be employed to scan the surface of the reticle for defects as a failsafe mechanism. In this manner, reticle manufacturers can realize an increase in quality assurance and throughput.

Figure 8:
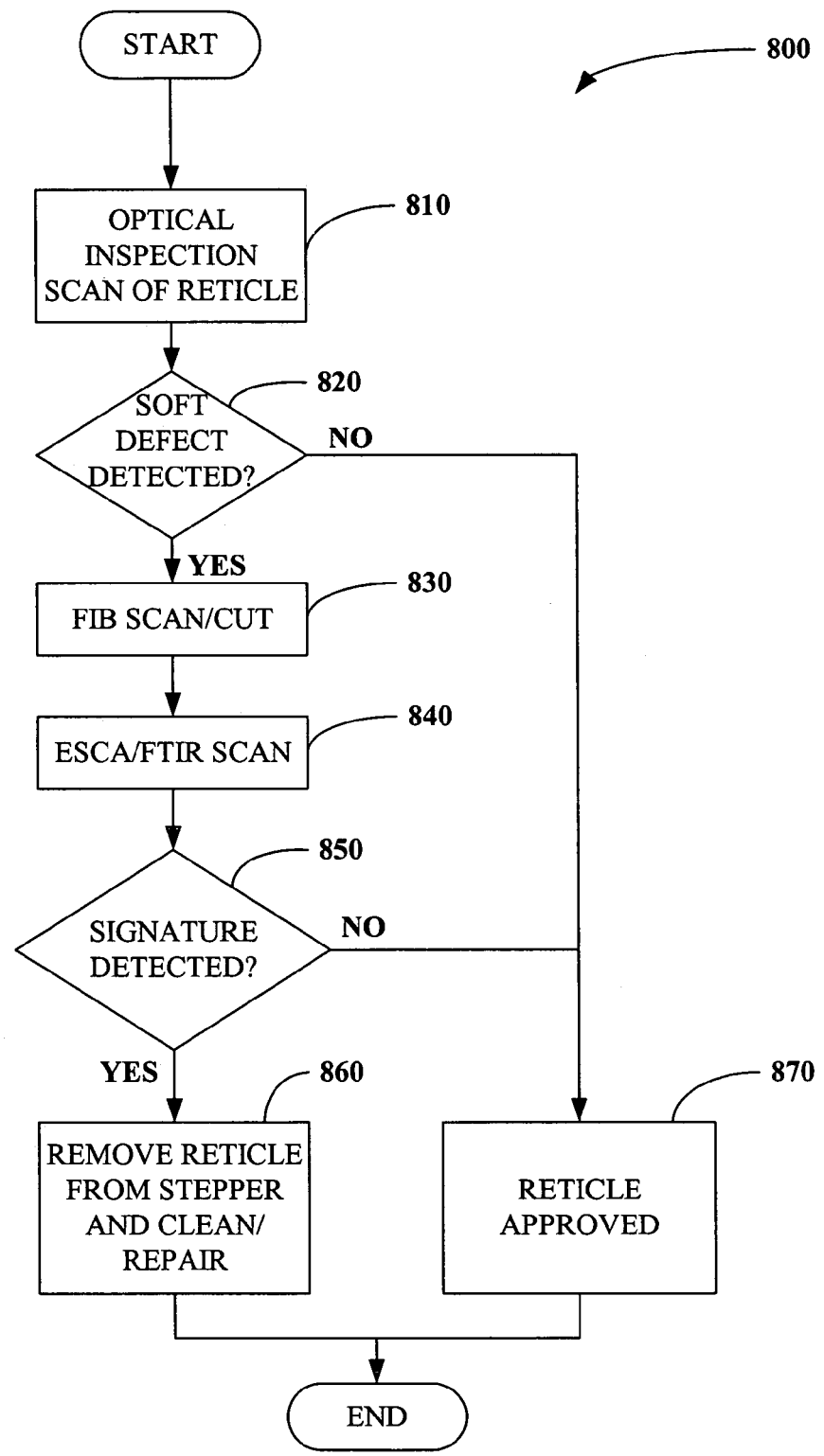
FIG. 8 is an illustration of a flow diagram of a methodology for inspecting and/or analyzing soft defects on a reticle in accordance with an aspect of the invention.

FIG. 8 is an illustration of a methodology 800 for inspecting a reticle in accordance with an aspect of the invention, which facilitates making an educated decision regarding whether to expend resources associated with cleaning a reticle based on signature presence. Beginning at 810, an SEM scans the reticle to determine whether a soft defect exists. At 820, a determination of the existence of a reticle soft defect is made. If a soft defect is not detected, then the method proceeds to 870 and approves the reticle. If a soft defect is present, an FIB can be employed to scan and/or cut the defect at 830. The scanning act permits the acquisition of further information regarding the defect, while the cutting act creates a clean surface for chemical analysis scan, which occurs at 840. Once the chemical analysis scan has been performed, the system has all the information required to make a determination regarding whether the defect is detrimental or not (e.g., whether the soft defect comprises a detrimental signature). At 850, if the information indicates that the size, position, composition, etc., of the defect is not detrimental to the performance of the reticle, then the method proceeds to 870 and Advanced Process Control can be initiated. If, at 850, the information indicates that a sulfur signature is present and will potentially detrimentally affect the performance of the reticle, then the method proceeds to 860, where the reticle is removed for repair and/or cleaning.

Figure 9:
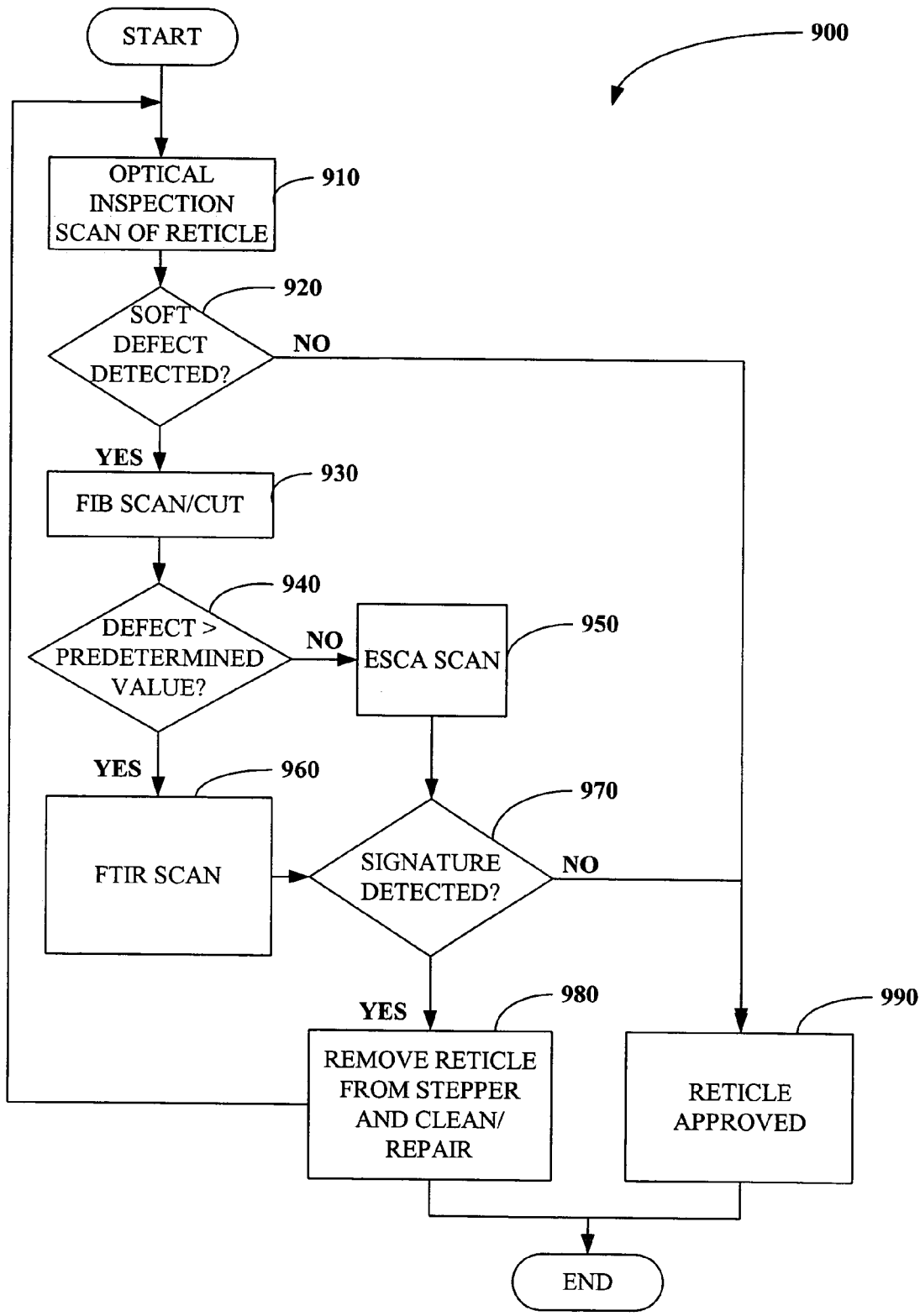
FIG. 9 is an illustration of a flow diagram of a methodology for inspecting and/or analyzing a soft defect on reticle in accordance with an aspect of the invention.

FIG. 9 is an illustration of a methodology 900 for inspection and/or correction of a soft defect in accordance with an aspect of the invention, in which the chemical analysis component is an ESCA and/or FTIR, depending on the size of the soft defect as determined from information gathered during the SEM and/or FIB scans. According to this methodology, the reticle is scanned by the SEM at 910. At 920, a determination is made as to the existence of a soft defect based on information gathered during the SEM scan. If a defect is not detected, the method proceeds to 990, where the reticle is approved. If the information gathered during the SEM scan indicates that a soft defect is present at 920, then the system directs the FIB to take action at 930. The action taken at 930 can be a scan or a cut, or both, depending on a determination of what action is required. Once the FIB action is completed, a determination is made at 940 regarding the size of the defect based on information gathered during the SEM and/or FIB scans. If the defect is smaller than a predetermined value, for example less than 100 microns in diameter, then ESCA can be employed to analyze the chemical composition of the defect at 950. If the defect is larger than a predetermined value, for example greater than 100 microns in diameter, then FTIR can be employed to determine the chemical composition of the defect at 960. Based on information gathered up to this point, a determination is made regarding whether the defect is detrimental (e.g., comprises a sulfur signature) to the performance of the reticle at 970. If the defect will not potentially detrimentally impair the performance of the reticle, then the system proceeds to 990, where the reticle is approved as described above. If the system determines that a sulfur signature is present and will potentially impair the performance of the reticle, then the system proceeds to 980. At 980, a user is prompted to remove the reticle from the stepper for repair and/or cleaning.

Figure 10:
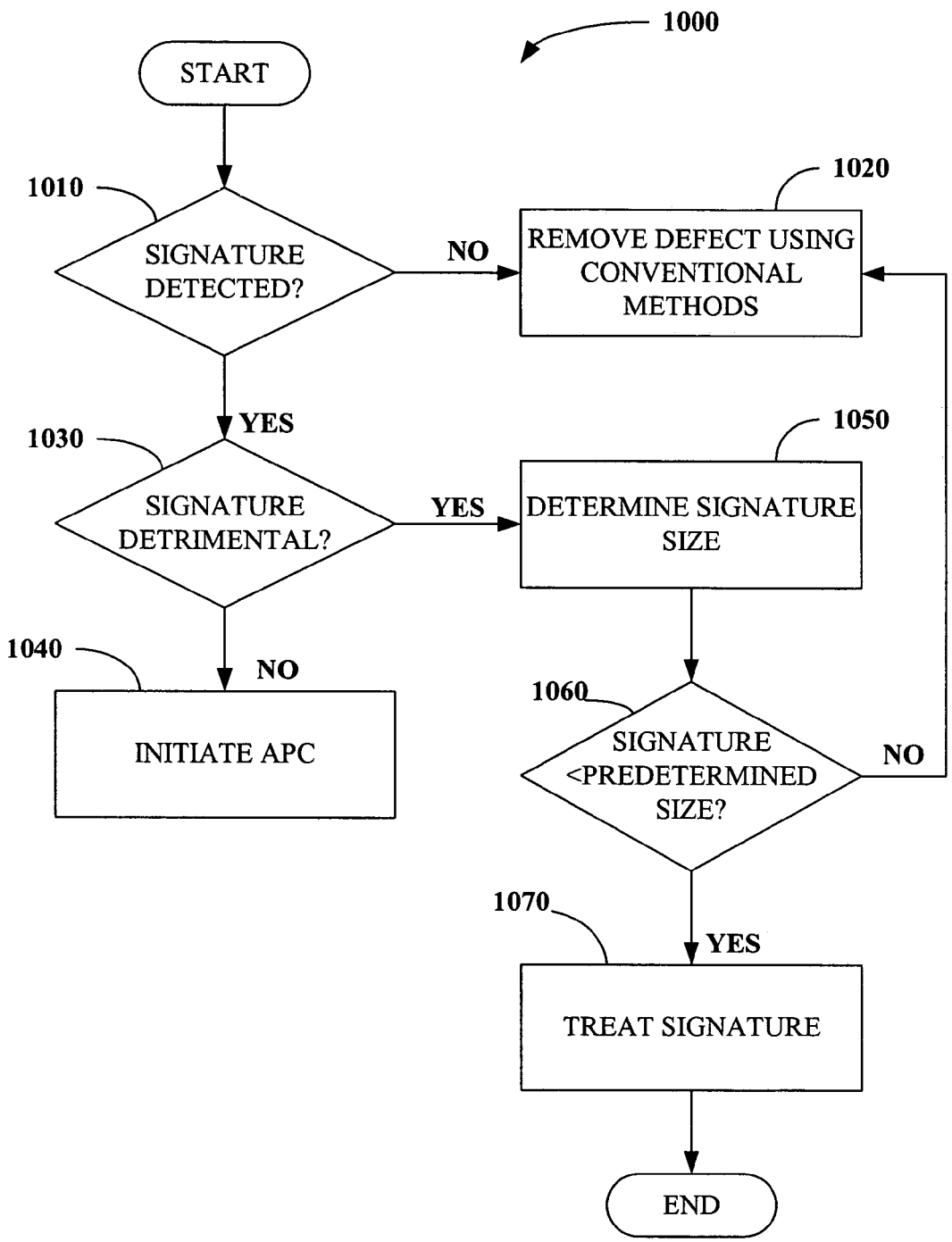
FIG. 10 is an illustration of a flow diagram of a methodology for inspecting, analyzing and/or treating a soft defect on a reticle in accordance with an aspect of the invention.

FIG. 10 is an illustration of a flow diagram of a methodology 1000 according to an aspect of the claimed invention. The method 1000 begins with a determination of whether a signature is present in a detected defect at 1010. The signature can be associated with, for example, sulfur, phosphorus, an amine group, etc. If no signature is detected, the system can remove the defect using conventional methods or remove the reticle for cleaning, etc., at 1020. If a signature is detected, the method proceeds to 1030 where a determination is made regarding whether the signature is detrimental to reticle performance. If the signature is not immediately detrimental, then Advanced Process Control (APC) can be initiated at 1040. If the signature is detrimental, then a determination is made regarding the size of the signature at 1050. At 1060, if the signature is larger than a predetermined threshold, then the method reverts to 1020 where the reticle is removed for cleaning, disposal, etc. If the signature is small (e.g., on the order of parts per billion), then the reticle can be placed in a non-reactive gas environment with continuous pump-out and converted into gaseous form via employing a FIB at 1070. In this manner, the present invention can advantageously mitigate the detrimental effects of a signature on reticle performance. However, it is to be appreciated that any detected signature is indicative of the existence of a signature between the reticle and pellicle.

Figure 11:
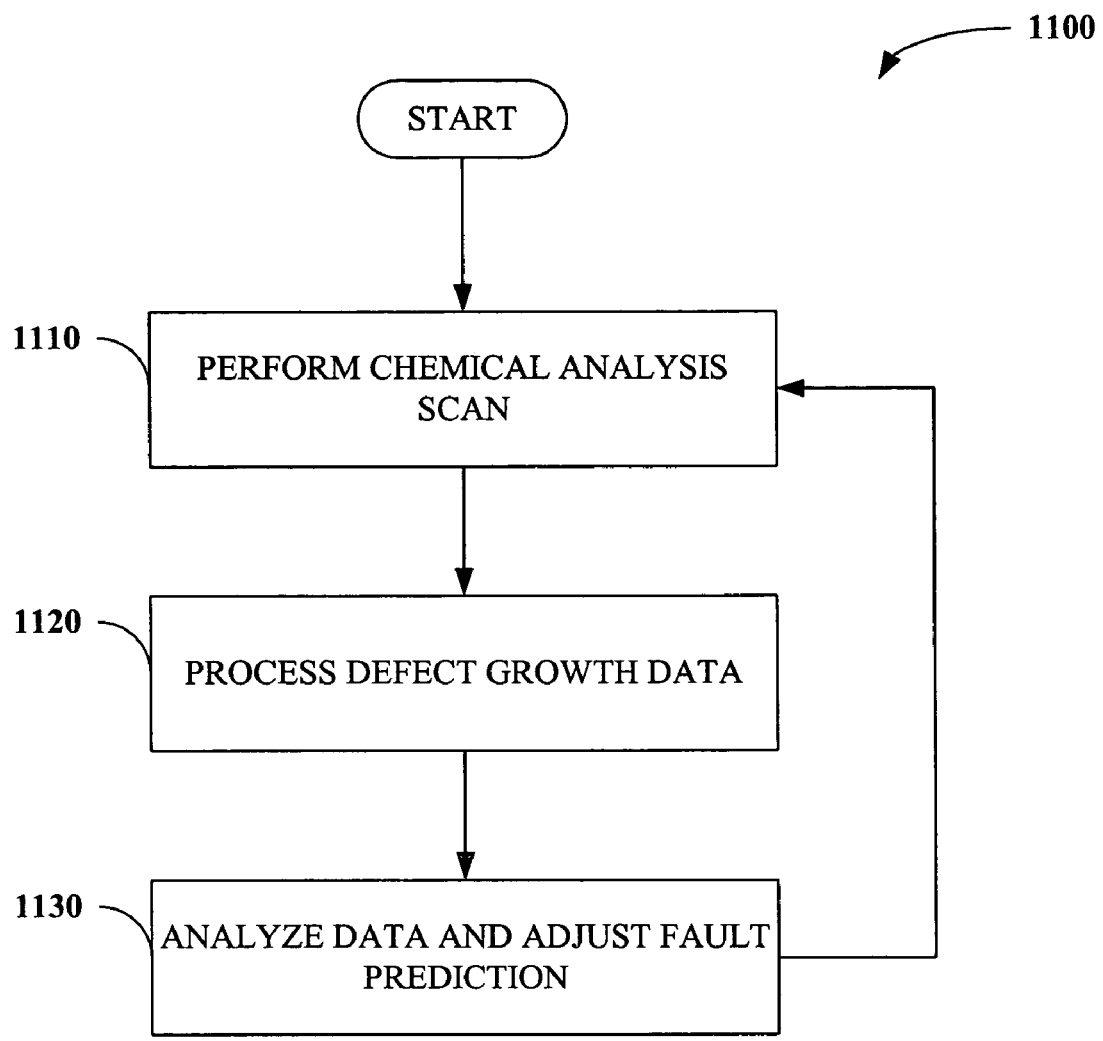
FIG. 11 is an illustration of a flow diagram of a methodology for inspecting and/or analyzing a soft defect a reticle via employing closed-loop feedback in accordance with an aspect of the invention.

FIG. 11 illustrates a methodology 1100 in accordance with an aspect of the present invention whereby closed loop feedback is employed. Upon determining that a soft defect comprising a signature is not immediately detrimental to reticle performance, a scan of the defect can be performed at 1110. Scans can be repeated at predetermined intervals to monitor soft defect growth during the lifetime of the reticle. For example, scans can be taken every 100,000 exposures. Data associated with defect growth can be processed at 1120. At 1130, data associated with defect growth is analyzed to facilitate predicting a temporal point at which the defect will produce a fault state. The method then returns to 1110, where a new scan of the defect is performed. This aspect of the invention advantageously permits a more educated decision regarding resource expenditures associated with maximizing throughput.

Figure 12:
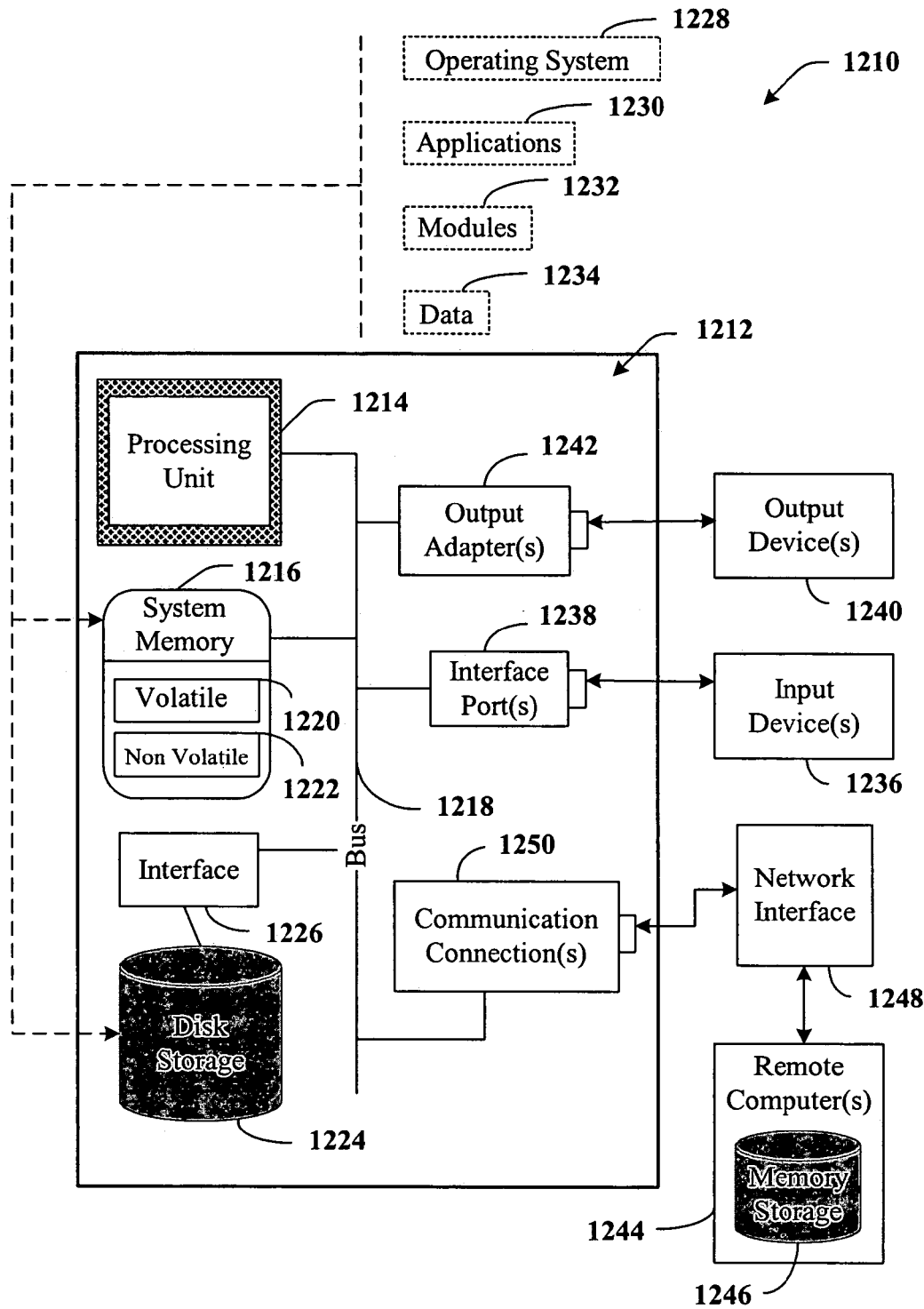
FIGS. 12 and 13 are illustrations of exemplary computing systems and/or environments in connection with facilitating employment of the subject invention.
Figure 13:
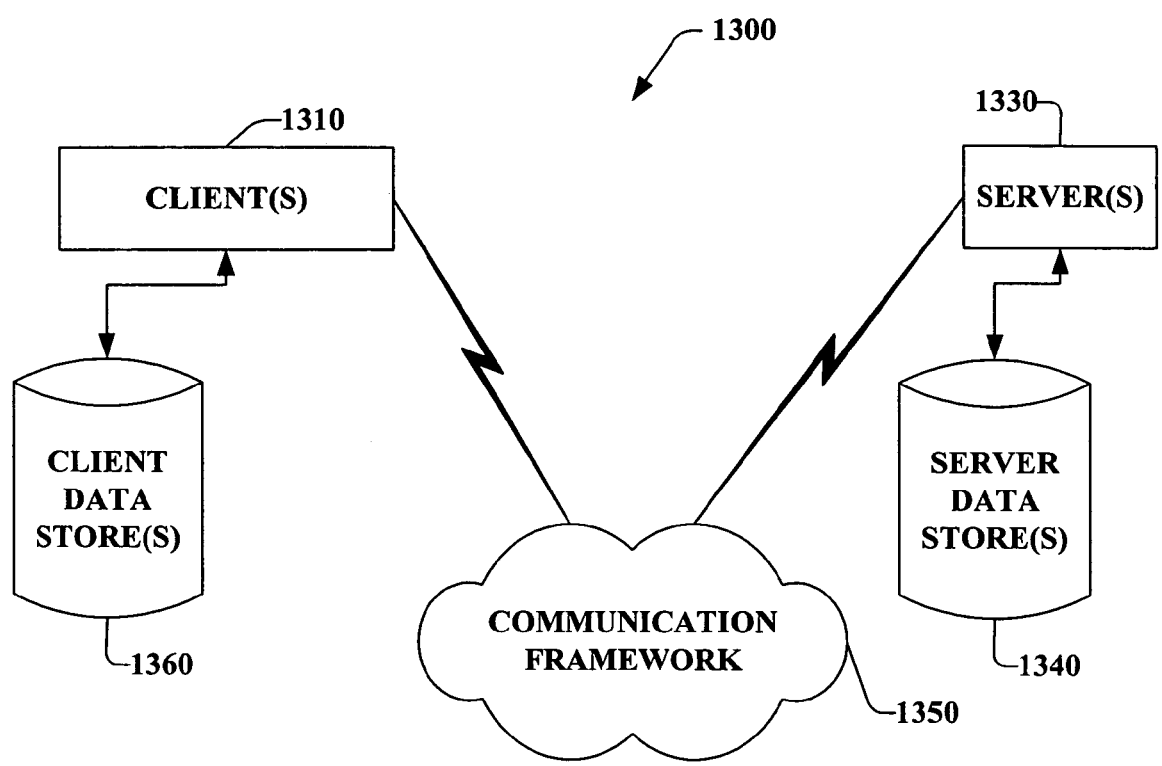

In order to provide a context for the various aspects of the invention, FIGS. 12 and 13 as well as the following discussion are intended to provide a brief, general description of a suitable computing environment in which the various aspects of the present invention can be implemented. While the invention has been described above in the general context of computer-executable instructions of a computer program that runs on a computer and/or computers, those skilled in the art will recognize that the invention also can be implemented in combination with other program modules. Generally, program modules include routines, programs, components, data structures, etc. that perform particular tasks and/or implement particular abstract data types. Moreover, those skilled in the art will appreciate that the inventive methods can be practiced with other computer system configurations, including single-processor or multiprocessor computer systems, mini-computing devices, mainframe computers, as well as personal computers, hand-held computing devices, microprocessor-based or programmable consumer electronics, and the like. The illustrated aspects of the invention can also be practiced in distributed computing environments where task are performed by remote processing devices that are linked through a communications network. However, some, if not all aspects of the invention can be practiced on stand-alone computers. In a distributed computing environment, program modules can be located in both local and remote memory storage devices.

With reference to FIG. 12, an exemplary environment 1210 for implementing various aspects of the invention includes a computer 1212. The computer 1212 includes a processing unit 1214, a system memory 1216, and a system bus 1218. The system bus 1218 couples system components including, but not limited to, the system memory 1216 to the processing unit 1214. The processing unit 1214 can be any of various available processors. Dual microprocessors and other multiprocessor architectures also can be employed as the processing unit 1214.

The system bus 1218 can be any of several types of bus structure(s) including the memory bus or memory controller, a peripheral bus or external bus, and/or a local bus using any variety of available bus architectures including, but not limited to, 11-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Universal Serial Bus (USB), Advanced Graphics Port (AGP), Personal Computer Memory Card International Association bus (PCMCIA), and Small Computer Systems Interface (SCSI).

The system memory 1216 includes volatile memory 1220 and nonvolatile memory 1222. The basic input/output system (BIOS), comprising the basic routines to transfer information between elements within the computer 1212, such as during start-up, is stored in nonvolatile memory 1222. By way of illustration, and not limitation, nonvolatile memory 1222 can include read only memory (ROM), programmable ROM (PROM), electrically programmable ROM (EPROM), electrically erasable ROM (EEPROM), or flash memory. Volatile memory 1220 includes random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

Computer 1212 also includes removable/non-removable, volatile/non-volatile computer storage media. FIG. 12 illustrates, for example a disk storage 1224. Disk storage 1224 includes, but is not limited to, devices like a magnetic disk drive, floppy disk drive, tape drive, Jaz drive, Zip drive, LS-100 drive, flash memory card, or memory stick. In addition, disk storage 1224 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1224 to the system bus 1218, a removable or non-removable interface is typically used such as interface 1226.

It is to be appreciated that FIG. 12 describes software that acts as an intermediary between users and the basic computer resources described in suitable operating environment 1210. Such software includes an operating system 1228. Operating system 1228, which can be stored on disk storage 1224, acts to control and allocate resources of the computer system 1212. System applications 1230 take advantage of the management of resources by operating system 1228 through program modules 1232 and program data 1234 stored either in system memory 1216 or on disk storage 1224. It is to be appreciated that the present invention can be implemented with various operating systems or combinations of operating systems.

A user enters commands or information into the computer 1212 through input device(s) 1236. Input devices 1236 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1214 through the system bus 1218 via interface port(s) 1238. Interface port(s) 1238 include, for example, a serial port, a parallel port, a game port, and a universal serial bus (USB). Output device(s) 1240 use some of the same type of ports as input device(s) 1236. Thus, for example, a USB port can be used to provide input to computer 1212, and to output information from computer 1212 to an output device 1240. Output adapter 1242 is provided to illustrate that there are some output devices 1240 like monitors, speakers, and printers, among other output devices 1240, which require special adapters. The output adapters 1242 include, by way of illustration and not limitation, video and sound cards that provide a means of connection between the output device 1240 and the system bus 1218. It should be noted that other devices and/or systems of devices provide both input and output capabilities such as remote computer(s) 1244.

Computer 1212 can operate in a networked environment using logical connections to one or more remote computers, such as remote computer(s) 1244. The remote computer(s) 1244 can be a personal computer, a server, a router, a network PC, a workstation, a microprocessor based appliance, a peer device or other common network node and the like, and typically includes many or all of the elements described relative to computer 1212. For purposes of brevity, only a memory storage device 1246 is illustrated with remote computer(s) 1244. Remote computer(s) 1244 is logically connected to computer 1212 through a network interface 1248 and then physically connected via communication connection 1250. Network interface 1248 encompasses communication networks such as local-area networks (LAN) and wide-area networks (WAN). LAN technologies include Fiber Distributed Data Interface (FDDI), Copper Distributed Data Interface (CDDI), Ethernet/IEEE 1102.3, Token Ring/IEEE 1102.5 and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1250 refers to the hardware/software employed to connect the network interface 1248 to the bus 1218. While communication connection 1250 is shown for illustrative clarity inside computer 1212, it can also be external to computer 1212. The hardware/software necessary for connection to the network interface 1248 includes, for exemplary purposes only, internal and external technologies such as, modems including regular telephone grade modems, cable modems and DSL modems, ISDN adapters, and Ethernet cards.

FIG. 13 is a schematic block diagram of a sample-computing environment 1300 with which the present invention can interact. The system 1300 includes one or more client(s) 1310. The client(s) 1310 can be hardware and/or software (e.g., threads, processes, computing devices). The system 1300 also includes one or more server(s) 1330. The server(s) 1330 can also be hardware and/or software (e.g., threads, processes, computing devices). The servers 1330 can house threads to perform transformations by employing the present invention, for example. One possible communication between a client 1310 and a server 1330 can be in the form of a data packet adapted to be transmitted between two or more computer processes. The system 1300 includes a communication framework 1350 that can be employed to facilitate communications between the client(s) 1310 and the server(s) 1330. The client(s) 1310 are operably connected to one or more client data store(s) 1360 that can be employed to store information local to the client(s) 1310. Similarly, the server(s) 1330 are operably connected to one or more server data store(s) 1340 that can be employed to store information local to the servers 1330.

What has been described above includes examples of the present invention. It is, of course, not possible to describe every conceivable combination of components or methodologies for purposes of describing the present invention, but one of ordinary skill in the art can recognize that many further combinations and permutations of the present invention are possible. Accordingly, the present invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system that facilitates soft defect detection and analysis on a reticle, comprising:
    a scanning component that detects and images soft defects;
    a milling component that excises material at soft defect locations;
    an analysis component that determines whether a signature is present in the chemical composition of a soft defect; and
    an excising component that removes the signature by transforming the signature into gaseous form and removing the gaseous signature with a pumping system.

2. The system of claim 1, the reticle comprising a pellicle.

3. The system of claim 1, the signature is indicative of the presence of at least one of sulfur, phosphorus, and an amino group.

4. The system of claim 1, the scanning component comprising at least one of a Scanning Electron Microscope and a Focused Ion Beam.

5. The system of claim 1, the milling component comprising a Focused Ion Beam.

6. The system of claim 5, the Focused Ion Beam comprising at least one of a single-beam Focused Ion Beam and a dual-beam Focused Ion Beam.

7. The system of claim 1, the analysis component comprising at least one of an Electron Microscope for Chemical Analysis and a Fourier Transform Infrared Spectroscope.

8. The system of claim 1, further comprising:
    a processor operatively coupled to the scanning, milling, and analysis components for sending and receiving information to and from the components; and
    a memory operatively coupled to the processor for storing information received and sent by the processor.

9. The system of claim 8, the memory comprising at least one of volatile and non-volatile memory.

10. The system of claim 8, further comprising a feedback loop between the processor and at least one of the scanning, milling, and analysis components that facilitates predicting soft defect growth with respect to time.

11. A method that facilitates soft defect detection and analysis on a reticle, comprising:
    scanning and imaging soft defects;
    milling detected soft defects to remove contaminants;
    analyzing detected soft defects to determine whether a signature is present in the chemical composition of the soft defects; and
    treating the signature by converting the signature into gaseous form and removing the transformed signature.

12. The method of claim 11, the reticle is scanned in a non-pellicle region.

13. The method of claim 11, the signature is indicative of the presence of at least one of sulfur, phosphorus, and an amino group.

14. The method of claim 11, the soft defect is scanned and imaged via employing at least one of a Scanning Electron Microscope and a Focused Ion Beam.

15. The method of claim 11, the soft defect is milled via employing a Focused Ion Beam.

16. The method of claim 11, the soft defect is analyzed via Electron Spectroscopy for Chemical Analysis if the soft defect is smaller than a predetermined size.

17. The method of claim 11, the soft defect is analyzed via Fourier Transform Infrared Spectroscopy if the soft defect is lager than a predetermined size.

18. The method of claim 11, further comprising making a determination as to whether a detected signature is detrimental to reticle performance.

19. The method of claim 11, further comprising employing closed-loop feedback to facilitate predicting soft defect growth with respect to time.

20. A method that facilitates treatment of a signature associated with a soft defect, comprising:
    employing a Focused Ion Beam in a non-reactive gas environment;
    effecting a phase shift in the signature present in the soft defect's chemical composition to a gaseous state; and
    providing a continuous pump-out of the gaseous signature to remove the signature in gaseous form.

21. A system that facilitates soft defect detection and analysis on a reticle, comprising:

means for scanning and imaging a soft defect;

means for milling the soft defect;

means for analyzing the soft defect to determine whether a signature is present in the chemical composition of the soft defect; and means for removing the signature by changing the signature into gaseous form and removing the gaseous signature.

22. The system of claim 21, further comprising means to determine whether the signature is indicative of the presence of at least one of sulfur, phosphorus, and an amino group.

23. The system of claim 21, further comprising:

means for processing information related to the detection and analysis of a soft defect; and means for storing information related to detection and analysis of a soft defect.

24. The system of claim 21, further comprising means for converting a signature to gaseous form for removal from the reticle.

* * * * *